(12) United States Patent
Zhang et al.

(10) Patent No.: US 9,430,040 B2
(45) Date of Patent: Aug. 30, 2016

(54) EYE GAZE DETECTION WITH MULTIPLE LIGHT SOURCES AND SENSORS

(71) Applicant: Microsoft Technology Licensing, LLC, Redmond, WA (US)

(72) Inventors: Zhengyou Zhang, Bellevue, WA (US); Anoop Gupta, Woodinville, WA (US); Qin Cai, Clyde Hill, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 219 days.

(21) Appl. No.: 14/154,542

(22) Filed: Jan. 14, 2014

(65) Prior Publication Data

US 2015/0199003 A1    Jul. 16, 2015

(51) Int. Cl.
*G09G 5/00*    (2006.01)
*G06F 3/01*    (2006.01)

(52) U.S. Cl.
CPC ..................................... *G06F 3/013* (2013.01)

(58) Field of Classification Search
None
See application file for complete search history.

(56) References Cited

U.S. PATENT DOCUMENTS

| | | | | |
|---|---|---|---|---|
| 2008/0211941 | A1* | 9/2008 | Deever | ................ H04N 5/2258 348/262 |
| 2013/0106681 | A1* | 5/2013 | Eskilsson | ................ G06F 3/013 345/156 |
| 2014/0052555 | A1* | 2/2014 | MacIntosh | ........... G06Q 20/208 705/23 |
| 2014/0145935 | A1* | 5/2014 | Sztuk | ..................... G06F 3/013 345/156 |

FOREIGN PATENT DOCUMENTS

| | | | |
|---|---|---|---|
| EP | 2521007 A1 | 11/2012 | |
| EP | 2649932 A1 | 10/2013 | |
| JP | 2649932 A1 * | 10/2013 | ............. A61B 3/113 |

OTHER PUBLICATIONS

"International Search Report and Written Opinion Issued in PCT Application No. PCT/US2015/011289", Mailed Date: Apr. 14, 2015, 10 Pages.
Second Written Opinion Issued in PCT Application No. PCT/US2015/011289, Mailed Date: Dec. 22, 2015, 9 Pages.

* cited by examiner

*Primary Examiner* — Ilana Spar
*Assistant Examiner* — Kirk Hermann
(74) *Attorney, Agent, or Firm* — Steve Wight; Sandy Swain; Micky Minhas

(57) ABSTRACT

The subject disclosure is directed towards eye gaze detection based upon multiple cameras and/or light sources. The cameras and/or light sources are configured to provide eye gaze detection for a device display at different orientations, at different tilt angles, at different user positions, at different user distances, and so on. Also described is a controller that selectively controls light source power and camera on/off state to provide images of the eye having sufficient quality for eye gaze detection and/or to conserve power.

20 Claims, 12 Drawing Sheets

EYE GAZE DETECTION WITH MULTIPLE LIGHT SOURCES AND SENSORS

BACKGROUND

As computers including mobile devices, handheld devices and related technology such as displays have evolved, human input mechanisms have similarly advanced. Natural user interfaces such as based upon speech recognition, head and skeletal tracking and gesture detection are becoming more widespread to supplement or in some cases replace keyboard, pointing device (mouse or stylus) and/or recognized symbol/handwriting input.

Eye gaze detection is another natural user interface technology. Eye gaze detection is desirable for natural multi-modal human-computer interaction, among other reasons.

With respect to computer displays, existing eye gaze detection endeavors have a very limited working space, such as having a small box around a calibration position in front of the display, with an eye gaze tracker needing to be placed below the display. Such technology thus has limited usage, because it is not particular useable in many situations, including in mobile computing scenarios which are becoming more and more prevalent.

SUMMARY

This Summary is provided to introduce a selection of representative concepts in a simplified form that are further described below in the Detailed Description. This Summary is not intended to identify key features or essential features of the claimed subject matter, nor is it intended to be used in any way that would limit the scope of the claimed subject matter.

Briefly, various aspects of the subject matter described herein are directed towards eye gaze detection, including having a plurality of cameras positioned proximate a display, comprising a first camera on a first edge adjacent the display, and a second camera on a second edge adjacent the display, in which the second edge is not parallel to the first edge. At least one light source is configured to output light that generates corneal reflection data when reflected by an eye. The cameras are coupled to an image processing component to provide image data to the image processing component including captured corneal reflection data for use in eye gaze detection.

In one or more implementations, three or more infrared light sources are configured to output light that generates corneal reflection data when reflected by an eye. A plurality of infrared-sensitive cameras is configured to capture the corneal reflection data for use in eye gaze detection. The cameras may provide image data including captured corneal reflection data to an image processing component.

One or more aspects are directed towards receiving image data corresponding to images of a human eye captured by at least two cameras. The image data may be combined into eye feature data that is provided to a gaze detection algorithm. Based upon at least one of the images, power to a light source may be reduced or turned off, and/or a camera may be turned off.

Other advantages may become apparent from the following detailed description when taken in conjunction with the drawings.

BRIEF DESCRIPTION OF THE DRAWINGS

The present invention is illustrated by way of example and not limited in the accompanying figures in which like reference numerals indicate similar elements and in which.

DETAILED DESCRIPTION

Various aspects of the technology described herein are generally directed towards substantially increasing the working space of eye gaze detection, including by placing multiple infrared (IR) light sources (e.g., LEDs) and sensors (IR-sensitive cameras) around a display. Also provided is a computational approach that leverages any available detected information, regardless the number of LED reflections seen by a camera and the number of cameras that see the eyes.

As one benefit, eye gaze detection functions even when a device display is at any orientation relative to the user, which is desirable with tablets, mobile computing devices, smartphones and the like. Similarly, eye gaze detection is able to work at a wide range of angles. For example, eye gaze detection remains effective even when a user holds a device at any of various angles relative to the user's eyes, or a laptop (or even a fixed display) may have its screen at different angles relative to the user's eyes.

It should be understood that any of the examples herein are non-limiting. For example, any number of cameras and light sources may be positioned in any number of ways, and only a small number of the possible ways are exemplified herein. Moreover, the algorithms and the like used to detect eye gaze are only examples, and the technology described herein is independent of and not limited to any particular one, and further is able to be adapted as new algorithms are developed. As such, the present invention is not limited to any particular embodiments, aspects, concepts, structures, functionalities or examples described herein. Rather, any of the embodiments, aspects, concepts, structures, functionalities or examples described herein are non-limiting, and the present invention may be used various ways that provide benefits and advantages in eye gaze detection in general.

Figure 1:
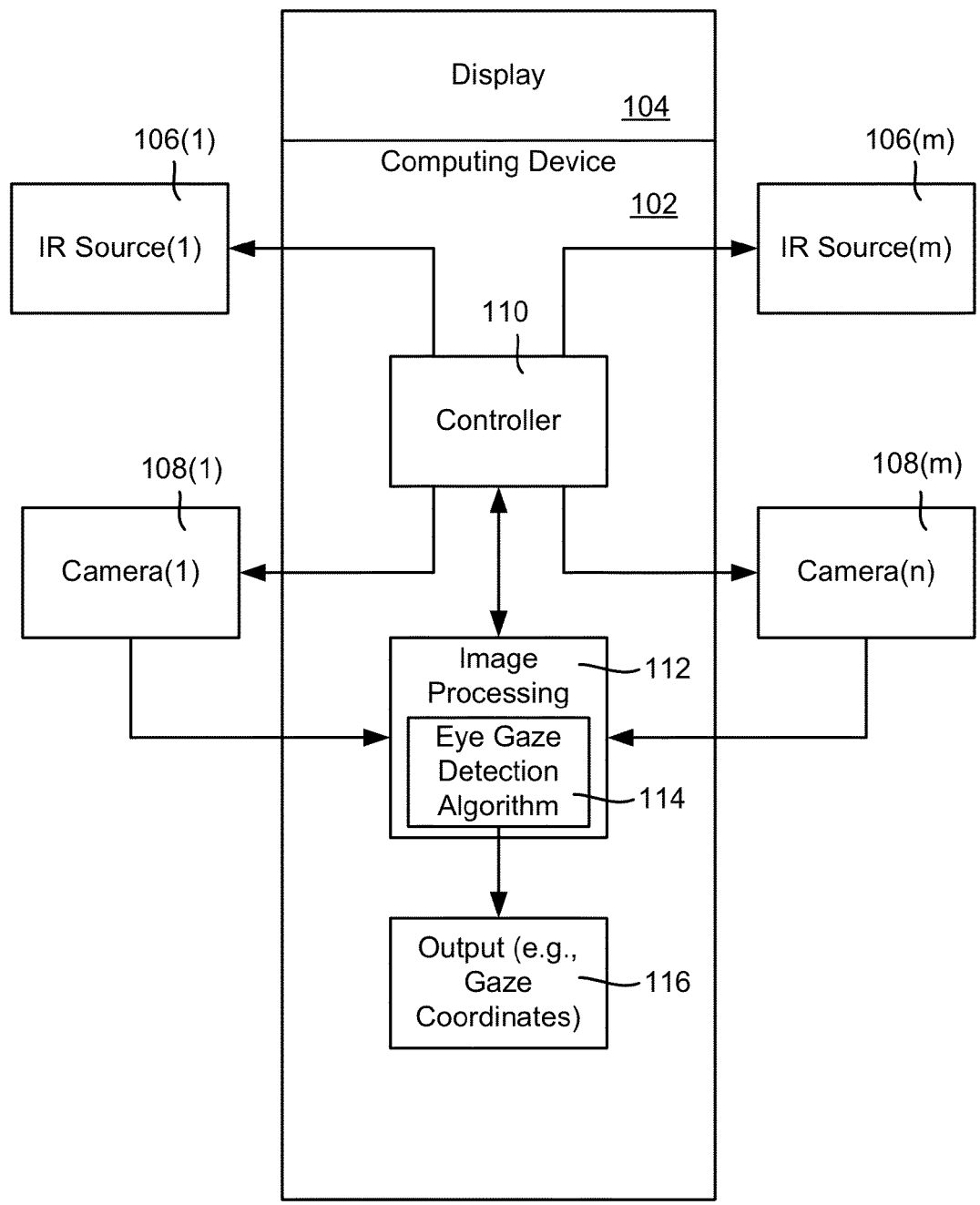
FIG. 1 is a block diagram illustrating example components that may be used in eye gaze detection, according to one or more example implementations.

FIG. 1 is a general block diagram illustrating example components that may be used to perform eye gaze detection. In FIG. 1, a computing device 102 and display 104 are shown. The display 104 may be an external display coupled to the computing device or a display incorporated into the computer device, e.g., its housing.

As shown in FIG. 1, a plurality of IR light sources 106(1)-106(m) is shown, along with a plurality of IR light-sensitive cameras 108(1)-108(n). The light sources may be individual light sources such as laser light emitting diodes (LEDs), and/or LEDs or the like that project through an optical element that diffracts/reflects the light, thereby providing a plurality of light sources. Note that any or all of the IR light-sensitive cameras may be combined with visible light cameras. Note further that the cameras may be attached to the device, e.g., embedded in the edges or physically coupled to the device, or may be external to the device, or a combination of both.

A controller 110 may be used to control the operation of the IR light sources 106(1)-106(m) and/or IR light-sensitive cameras 108(1)-108(n) as described below, although in one or more implementations the light sources and cameras may be "always-on" whereby no "controller" other than a power source presumably with on/off capabilities is needed. Note that IR light is used because it is not noticeable to humans, however in certain situations it may be desirable to use visible light, such as with the subject's eyes wearing contact lenses that block the particular visible light wavelength being used. Thus, as used herein, "light source" is not limited to IR wavelengths.

In general, the cameras 108(1)-108(n) capture images that are fed to an image processing component 112, including an eye gaze detection algorithm 114. The image processing component 112 provides an eye gaze detection output 116, such as gaze coordinates representative of where the user is currently gazing in the given frame or the like being processed. Such output 116 may be buffered, such as for use with other input (e.g., mouse clicks or gestures), may be consumed by an operating system (e.g., to move a cursor), may be used by an application (e.g., to highlight a menu item) and/or the like.

With respect to an eye gaze detection algorithm 114, any existing or to-be-developed algorithms may be employed, including combining the decisions of one or more, for example. In general, eye gaze detection algorithms work by detecting where the IR light sources reflect off of the eyeball.

In general, remote gaze tracking systems operate using the infrared light sources to generate corneal reflections, referred to as glints, which are captured as part of the subject's eye images. The captured images are processed to extract informative features that are invariant to illumination and viewpoint, such as pupil center, the corneal reflections (e.g., indicative of the eyeball's position) and/or limbus contour.

Basic constraints of one suitable algorithm are described in "*General Theory of Remote Gaze Estimation Using the Pupil Center and Corneal Reflections,*" Guestrin and Eizenman, IEEE TRANSACTIONS ON BIOMEDICAL ENGINEERING, VOL. 53, NO. 6, PAGES 1124-1133, (JUNE 2006), herein incorporated by reference. In general, two constraints for each LED are derived from the law of reflection. The first is that the light, its reflection point on the corneal, the camera center, and the corneal center are coplanar. The second is that the angle of incidence at the reflection point is equal to the angle of reflection.

As described therein, a one-time personal calibration is performed to determine each person's difference between the optical axis of the eye and the visual axis (gaze direction). When two LEDs are observed by a camera, the optical axis can be determined, and because of the calibration, the gaze direction as well.

However, the technology described herein is not limited to any particular gaze detection algorithm; rather, described herein is a unified framework for any number of cameras and any number of LEDs visible from each camera. Thus, any of various alternative algorithms may be employed.

Among the different types of algorithms/methods presently in use, interpolation-based methods directly map eye features to gaze points through 2D regression functions without considering the optical properties, the eye physiology, and the geometric relationship between eye, screen and camera. Therefore, interpolation-based methods are straightforward to implement, but sensitive to head movements, especially to depth variation. Model-based methods, such as provided in the above-described reference, estimate a 3D gaze vector and compute 2D points of interest by intersecting 3D rays with the 2D screen plane. Unlike interpolation-based methods, model-based methods are able to accommodate larger head movements, yet need calibration. Cross-ratio (CR)-based approaches do not require hardware calibration and allow free head motion, however at present, CR-based approaches are not particularly accurate. The technology described herein is independent of any particular algorithm or algorithms, and is not limited to any of those currently in existence.

FIGS. 2A-9 depict a number of possible examples including hardware configurations and aspects related thereto. In any of these example, it should be noted that the depicted sizes (device, display screen, cameras, LEDs), camera field-of-views and other representations are only for purposes of illustration, and are not intended to convey any specific information such as actual sizes, actual angles, actual distances, actual positions or the like.

Figure 2A:
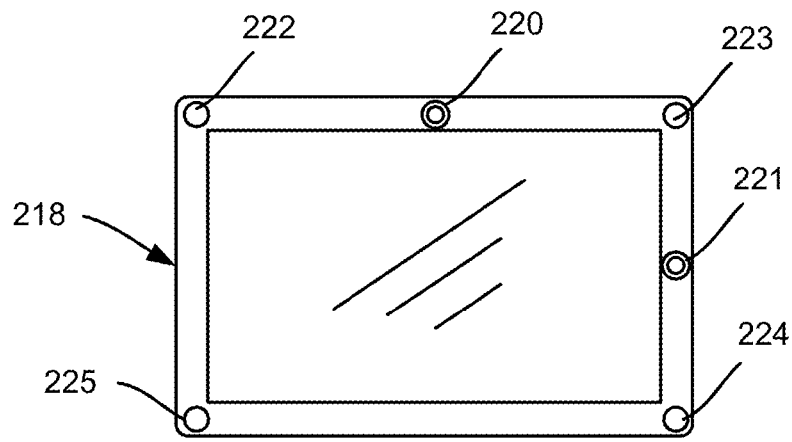
FIGS. 2A and 2B are example representations of cameras and light sources used in eye gaze detection, in which the cameras and light sources are positioned on (e.g., embedded into) device edges adjacent a display shown in different orientations, according to one or more example implementations.
Figure 2B:
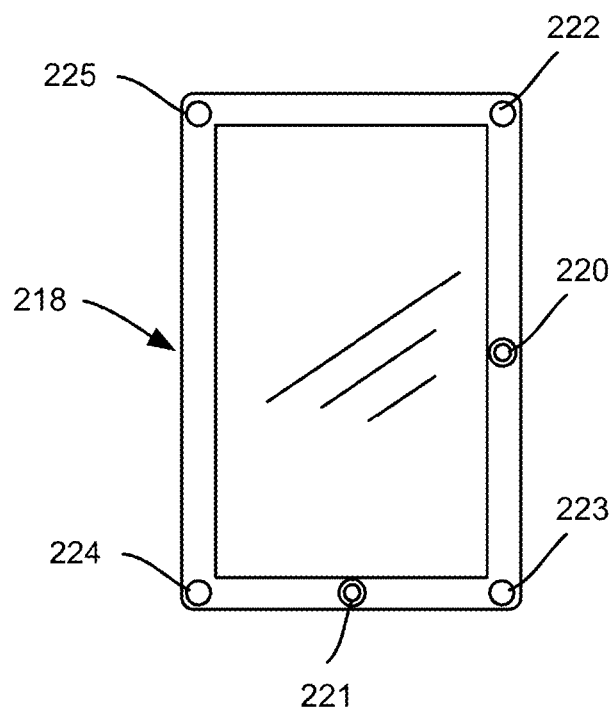

In one implementation, generally represented in FIGS. 2A and 2B, a device 218 comprises (at least) two cameras 220, 221 positioned on different edges of a display that are not parallel to one another; (horizontal and vertical edges are shown, however as can be readily appreciated, perpendicular edges are not required). Any number of light sources may be present, and need not be physically coupled to the display;

for purposes of illustration, four light sources 222-226 are shown, but even a single one may suffice. Note that a tablet-type device 218 is represented in FIGS. 2A and 2B for purposes of example, however any device capable of being oriented differently, such as a smartphone and/or a relatively fixed monitor that may be mounted vertically or horizontally, may similarly benefit.

As can be readily appreciated, because the cameras 221 and 222 are installed on different non-parallel edges, eye gaze detection still functions well regardless of the orientation of the display relative to the user, that is, good eye gaze detection exists whether the display is in landscape or portrait mode. Furthermore, more than one cameras increase the accuracy of eye gaze detection. Thus, the exemplified configuration may be used on a device (e.g., tablet, smartphone, television or monitor) having an incorporated display, in which the device is configured to change the rendering orientation of at least some of its displayed content output in conjunction with a current orientation of the device.

FIGS. 3A-5B are directed towards other aspects of using multiple cameras with gaze detection. Note that while a device 330 comprising a laptop device or device with tilt-able display relative to a keyboard or the like is shown for purposes of illustration, the concepts described with respect to FIGS. 3A-5B apply to any device having a screen that may be angled relative to a user's eyes (note that a single eye suffices), including tablets, smartphones, generally fixed monitors and the like.

Figure 3A:
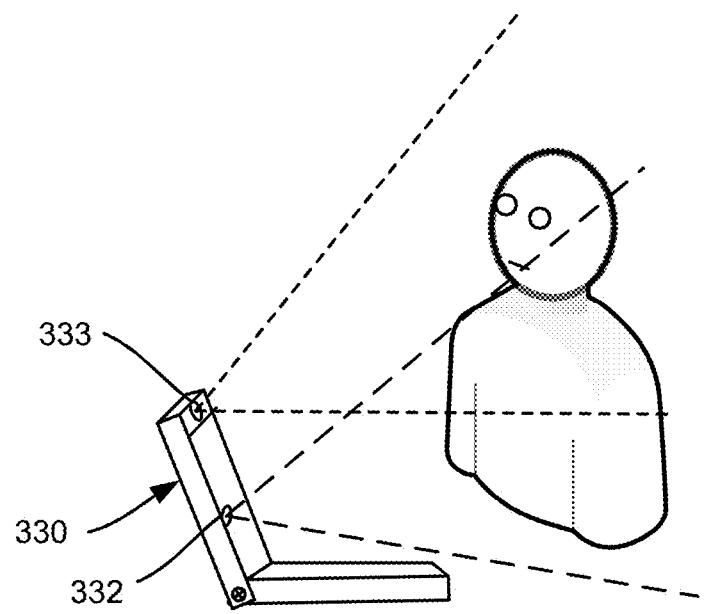
FIGS. 3A and 3B are example representations of angled cameras having different angles for capturing a user's eye or eyes at different relative user locations for use in eye gaze detection, according to one or more example implementations.
Figure 3B:
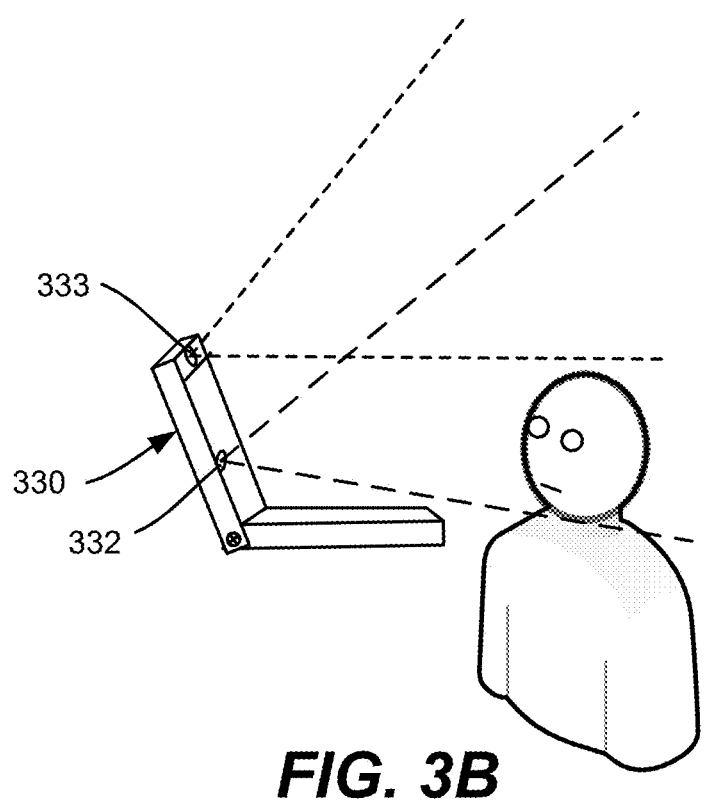

As shown in FIGS. 3A and 3B, the cameras need not be angled the same way, whereby a larger combined field-of-view is provided. For example, consider that in FIG. 3A, the tilt of the screen relative to a user's position is such that the user's eyes are generally above the field of view of a camera 332, while in FIG. 3B the tilt/user position is such that the user's eyes are generally below the field of view of a camera 333. As shown, however, by having two cameras 332 and 333 angled differently relative to one another, the user's eyes are always within the field of view of at least one of the cameras 332, 333 (at least while the user is at a reasonable distance from the display screen).

Figure 4A:
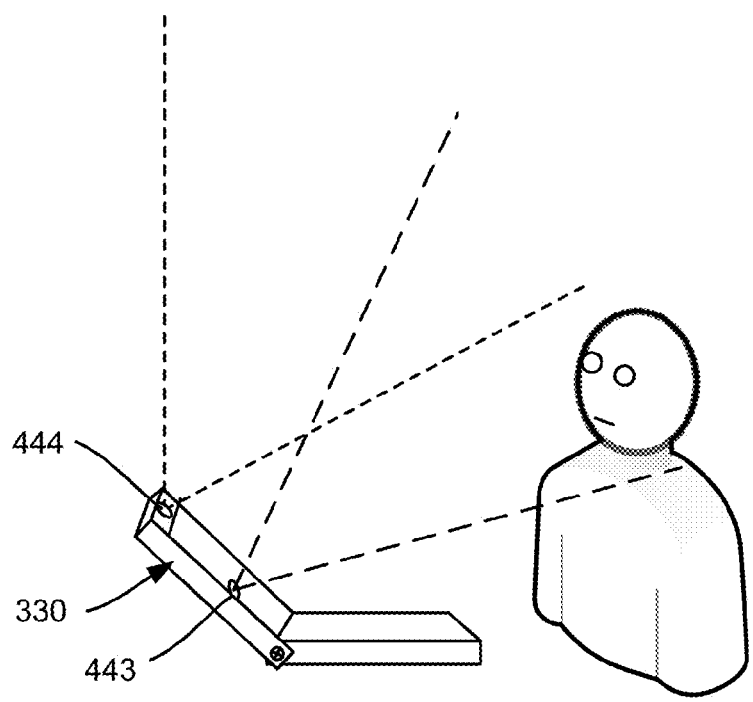
FIGS. 4A and 4B are example representations of angled cameras having different angles for capturing a user's eye or eyes at different display tilt positions, for use in eye gaze detection, according to one or more example implementations.
Figure 4B:
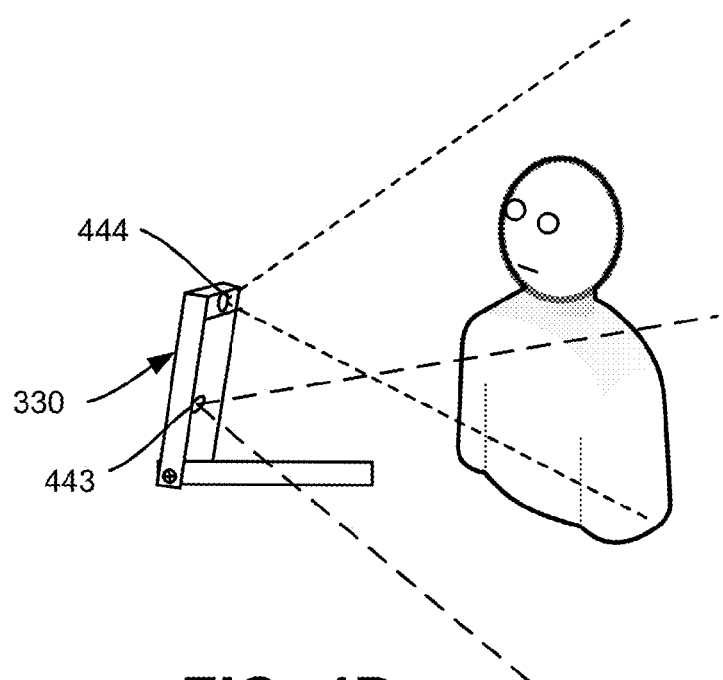

FIGS. 4A and 4B exemplify a similar concept to FIGS. 3A and 3B, namely how two cameras 443 and 444 angled differently (they may be the same angles/cameras as in FIGS. 3A and 3B) facilitate eye gaze detection with differing display tilts. In FIG. 4A, only one camera 443 captures images of the user's eyes because of the laptop tilt relative to the user's position. In FIG. 4B, the user has not moved relative to the device 330, although the tilt has changed; however because of the cameras' relative angles, the other camera 444 captures images of the user's eyes.

Figure 5A:
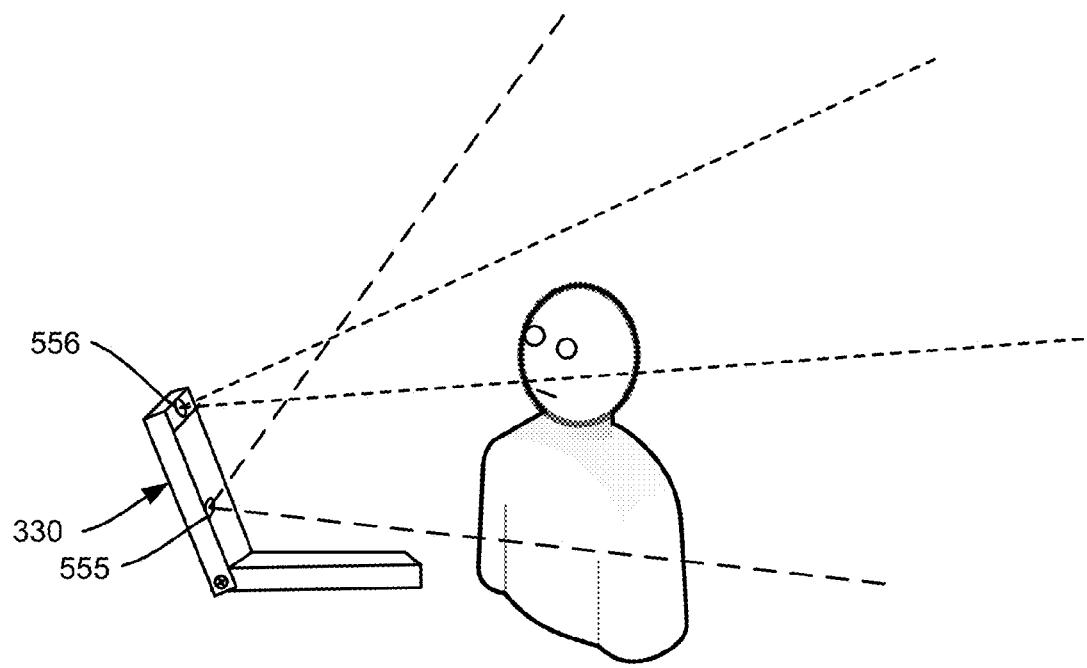
FIGS. 5A and 5B are example representations of cameras having different focal lengths for capturing a user's eye or eyes at different distances, for use in eye gaze detection, according to one or more example implementations.
Figure 5B:
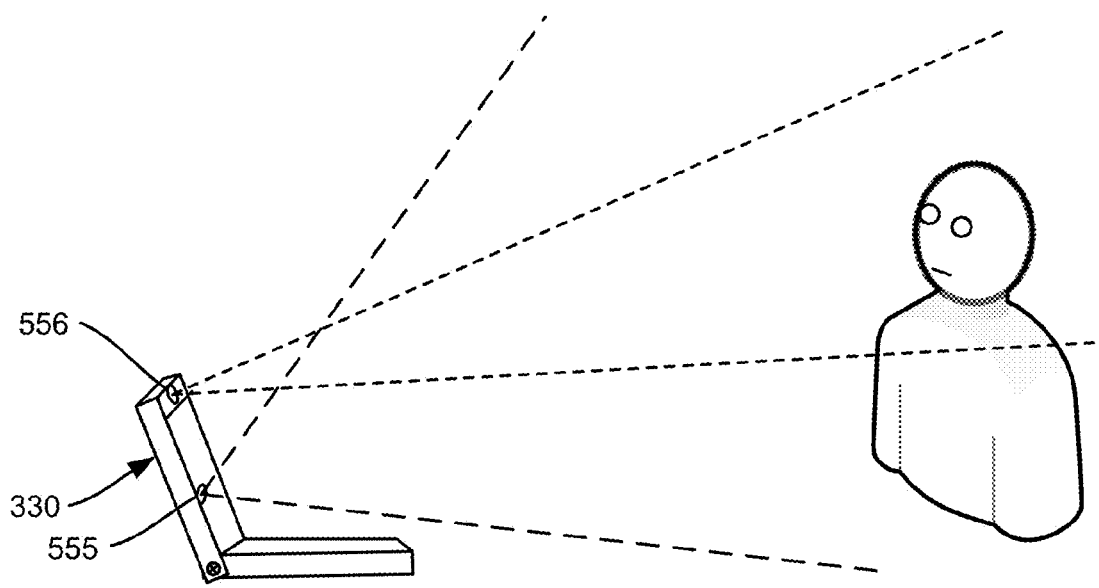

In another aspect, FIGS. 5A and 5B represent having cameras with different focal lengths. In general, if a user eyes are not at the proper focal length for a given camera, the captured images will not be sharp, whereby the eye features (e.g., glints) become more difficult to detect accurately.

In FIG. 5A, the user is close to the device, whereby one camera 555 obtains a sufficiently sharp image of the eyes. In FIG. 5B, the user is further away, whereby the other camera 556 obtains a sufficiently sharp image of the eyes. Also because a longer focal length is used (resulting a narrower field of view), there are still a sufficient number of pixels covering the eye region.

As can be readily appreciated, the concepts of FIGS. 3A-5B may be combined, using more cameras as appropriate. Thus, for example, a third camera at another angle can provide an image that works even with a severe tilt (e.g., FIG. 4A) and an unusually positioned user (e.g., FIG. 3B). Differently angled cameras may be combined with cameras having different focal lengths, e.g., four cameras can provide up to four different angles and four focal lengths, or any combination thereof, e.g., [camera angle A, focal length X], [camera angle B, focal length X], [camera angle A, focal length Y], [camera angle B, focal length Y]. Any practical number of cameras may be present in a given implementation.

Moreover, it should be noted that FIGS. 3A-5B show the cameras positioned on different edges. However, this is not needed; the two cameras in each example can be on a common edge if desired, separated as far apart as desired, e.g., at the edge corners or as close as possible to each other, or anywhere in between. Thus, it is understood that FIGS. 3A-5B are non-limiting examples only for the purposes of illustration.

Figure 6A:
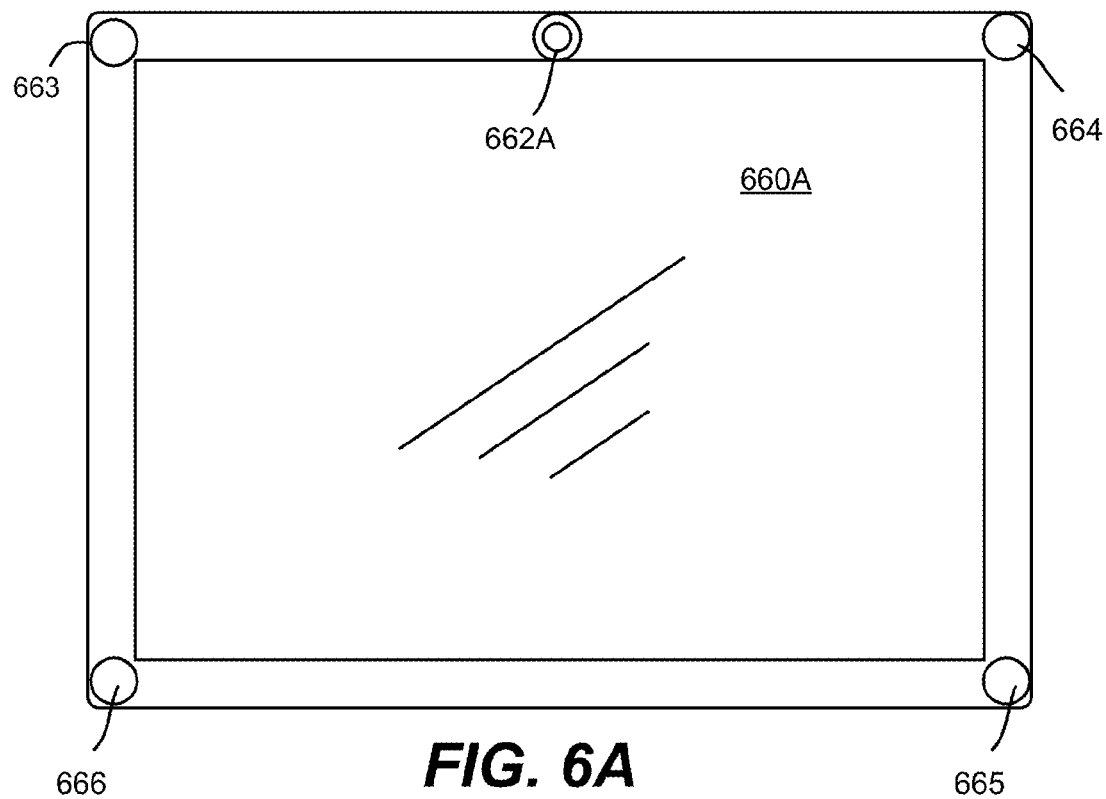
FIGS. 6A and 6B are example representations of example devices/displays having light sources positioned in different locations relative to the displays, for use in eye gaze detection, according to one or more example implementations.
Figure 6B:
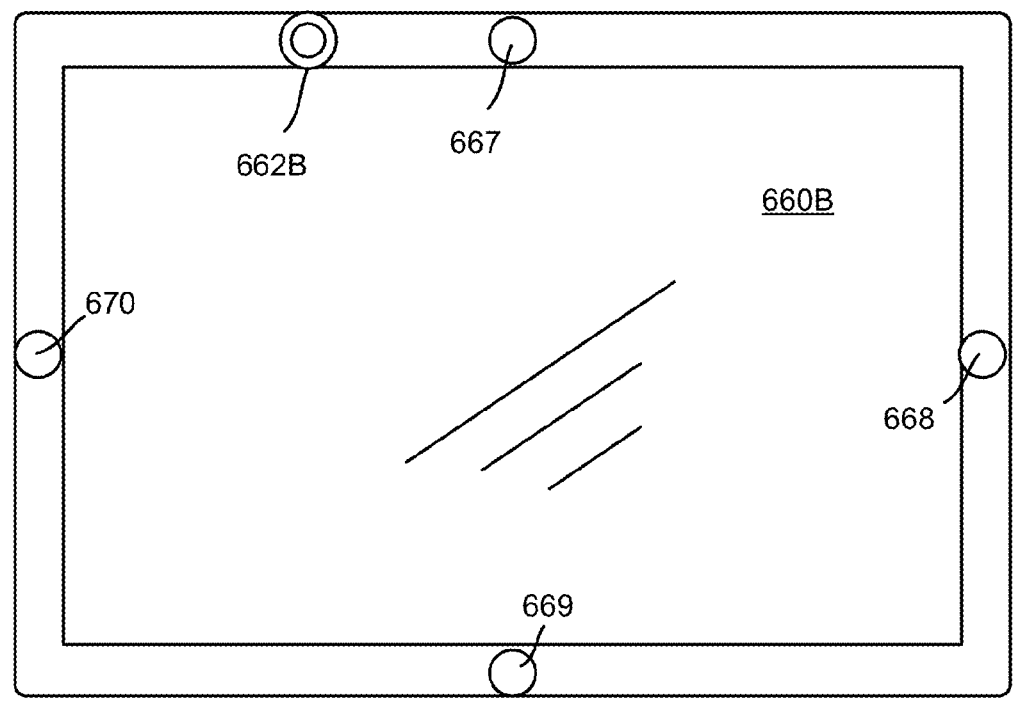

FIGS. 6A and 6B show an implementation with an IR LED light (at least one) on each side of a device display 660A and 660B, respectively; a camera 662A and 662B is also shown in each, although it is understood that there may be more than one camera, and that any camera position may be used; one or more cameras may be physically detached from the device. FIG. 6A shows four LEDs 663-666 at the corners. FIG. 6B shows four LEDs 667-670 each at the middle of a side edge.

Figure 7:
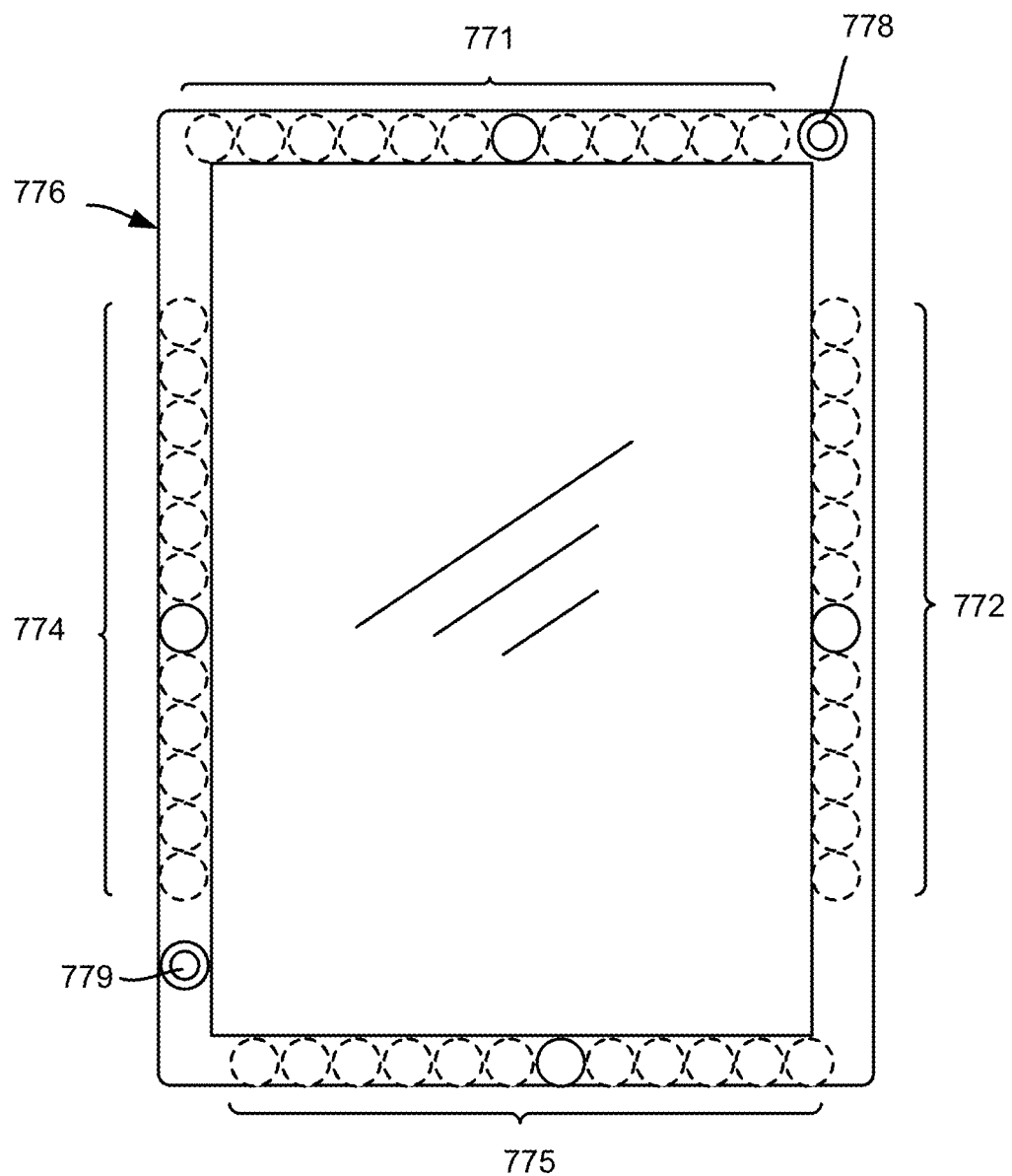
FIG. 7 is an example representation having an alternative arrangement of multiple light sources for use in eye gaze detection, according to one or more example implementations.

As can be readily appreciated, these are only examples, and other configurations with four or more LEDs may be used. FIG. 7 shows any number of four or more LED lights, such as arranged in bars of LED lights 771-774 embedded in a device 776 relative to each side of a display. Symmetry is not required. Cameras 778 and 779 are shown, although again this is only an example, and any number of attached or detached cameras may be present in a given implementation. Note that the LED lights represented as "dashed" circles in FIG. 7 may or may not be present in a given implementation, and/or more than those shown may be present.

Figure 8A:
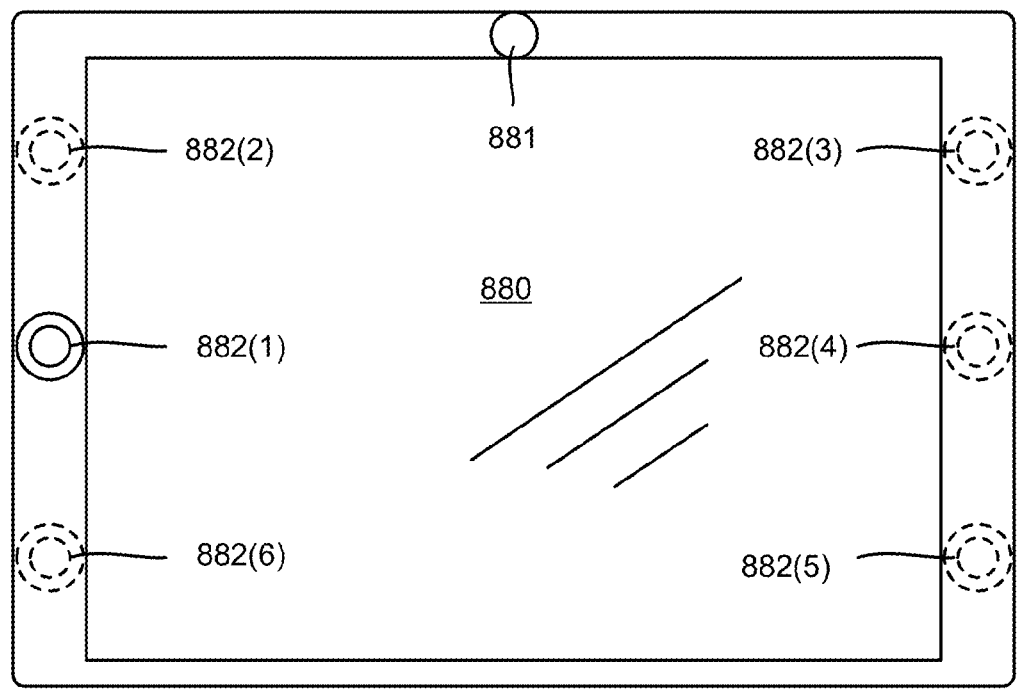
FIGS. 8A and 8B are example representations of example devices/displays demonstrating some possible numbers of cameras and/or light sources positioned proximate displays for use in eye gaze detection, according to one or more example implementations.
Figure 8B:
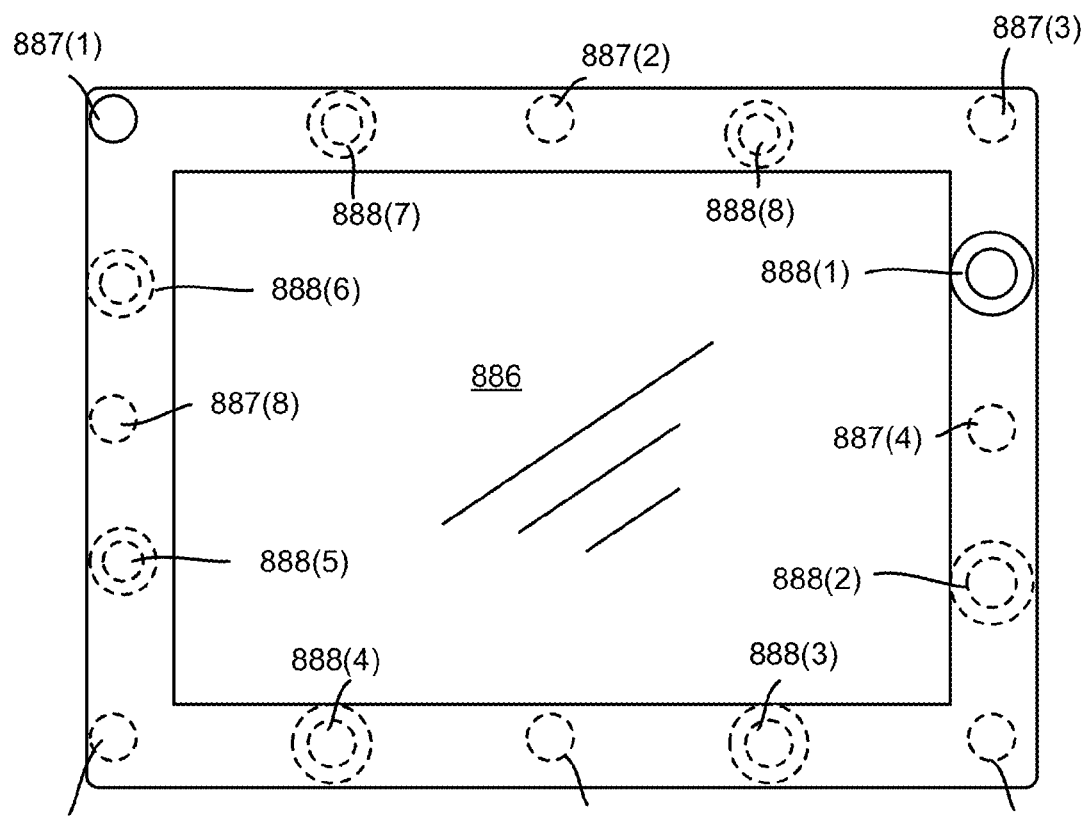

FIGS. 8A and 8B show two more of the possibly many configurations possible. FIG. 8A shows a device with display 880 having a single LED 881 and one or more (e.g., up to six in this example) cameras 882(1)-882(6). FIG. 8B shows a device with display 886 having one or more LEDs 887(1)-887(8) (e.g., up to eight in this example) and one or more (e.g., up to eight in this example) cameras 888(1)-888(8). As can be readily appreciated, these are just two of the many possible configurations that may be used for eye gaze detection as described herein.

Figure 9:
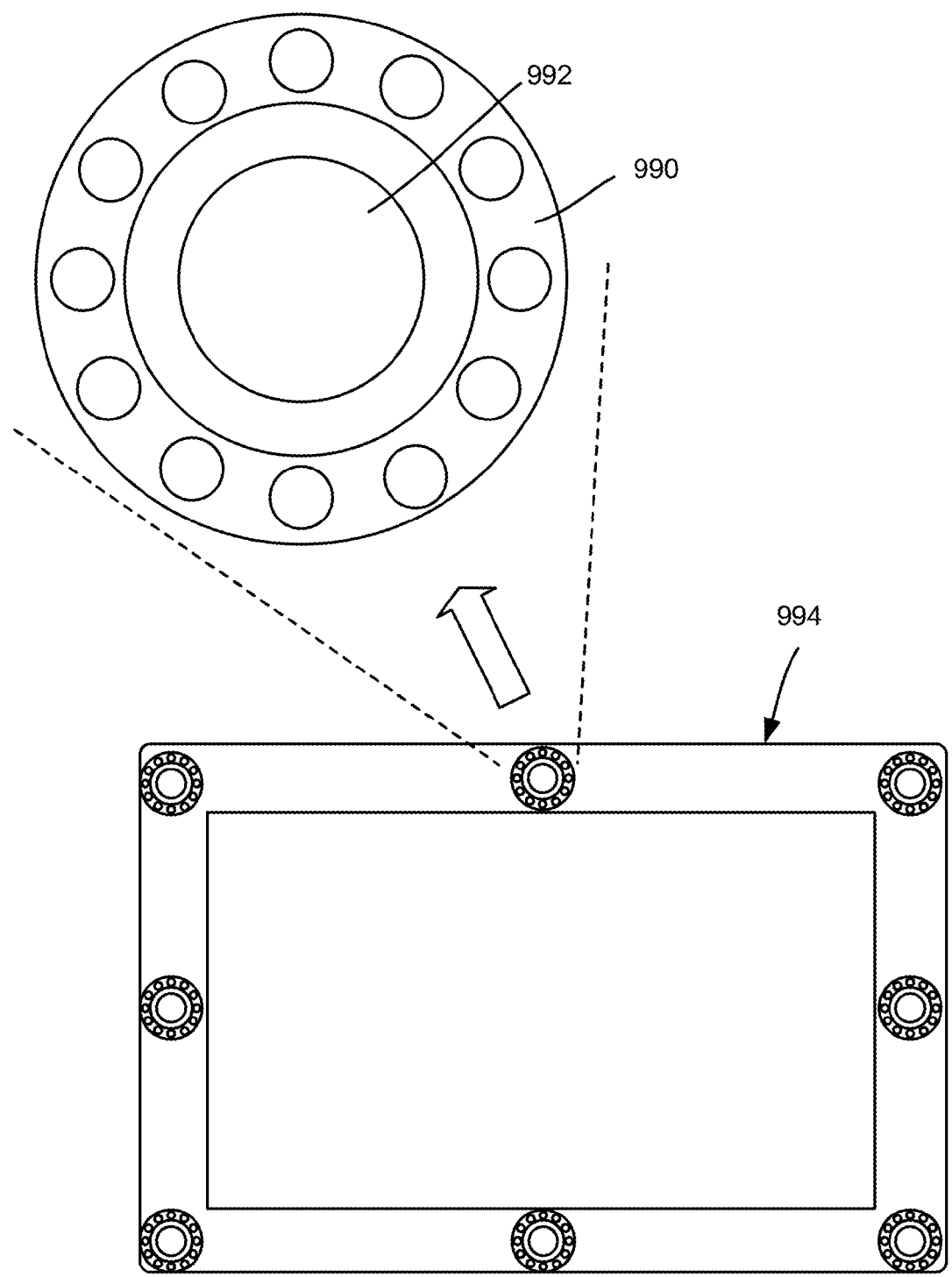
FIG. 9 is an example representation of a display, cameras and light sources for use in eye gaze detection, including an enlarged view of a camera surrounded by light sources, according to one or more example implementations.

FIG. 9 shows another alternative that may be used with any or all of the cameras/LEDs exemplified in FIGS. 2A-8B. In FIG. 9, there is shown (including in an enlarged view) a ring of IR LEDs 990 around a camera 992. As represented in FIG. 9, one or more these ring/camera assemblies may be placed on a device, such as the device 994. Although twelve generally symmetrical LEDs are illustrated in the ring 990, any practical number may be present, e.g., two or more may suffice, and symmetry is not required. Note that light sources arranged to surround a light source may not necessarily form a "ring" in the conventional sense, and thus "surround" refers to any such configuration, whether in the form of a ring or not.

The exemplified ring 990 of LEDs can be turned on or off, such as in synchronization with image capture. Note that when the ring 990 of LEDs is on illuminating a subject's eye, the pupil appears bright (bright eye effect), generally making pupil detection and pupil estimation easier and more accurate. Note that bright pupil and dark pupil techniques may be combined.

Turning to aspects related to control, cameras can be selectively turned on or off and/or IR LEDs may be turned on or off or varied in intensity, such as to save energy, and/or to obtain higher quality images under current conditions. Head tracking, position sensing, actual image processing and/or the like may be used to save energy and/or obtain higher quality images, for example. Initial and occasional sampling measurements may be used to determine settings to use that provide sufficient quality images with less than full power when possible, for example.

For example, when in landscape viewing mode, only the cameras below (or above) the display may be turned on while others are turned off. Further, if multiple cameras exist on the same edge, then less than all on that edge may be needed. For example, consider two cameras below a display, with the person's head positioned on the right side. The left camera may be turned off, as it is unlikely that the left camera will see the person's head, as least not as well as the right camera.

In the example of differently angled cameras only the camera that is obtaining an eye image may be turned on. Head tracking may be used to determine which camera(s) will capture the eye, although image processing may be similarly used to determine whether an eye is present in an image. For different focal length cameras, only the one that is sufficiently sharp may be turned on. For example, initially all cameras may be used, but sharpness detection in the images relative to the eye may determine which to use.

Further, when multiple images are present, the image data from the multiple cameras may be combined, such as averaged or via a weighted averaging technique. For example, in the above sharpness detection scenario, consider that both cameras detect the eye. The eye position computed via the glints detected in one image may be averaged with the eye position computed via the glints detected in the other image; the sharper of the two images may be given more weight commensurate with the sharpness, for example.

The intensity of each LED light can be adjusted. For example, in an environment with stronger ambient IR light, the intensity of LED lights can be increased. Other ambient light sensors, as well as actual image processing, may be used to adjust the LED intensity. Different IR wavelengths may be used. IR lights may be pulsed to save energy, such as in coordination with camera capturing. IR lights may be pulsed with a signature, and/or used with subtraction to obtain useable images in brighter ambient light.

LEDs also can be turned on or off when needed. For example, LEDs may generate additional reflections on eyeglasses. Such LEDs that cause reflections on eyeglasses into cameras may be turned off.

Figure 10:
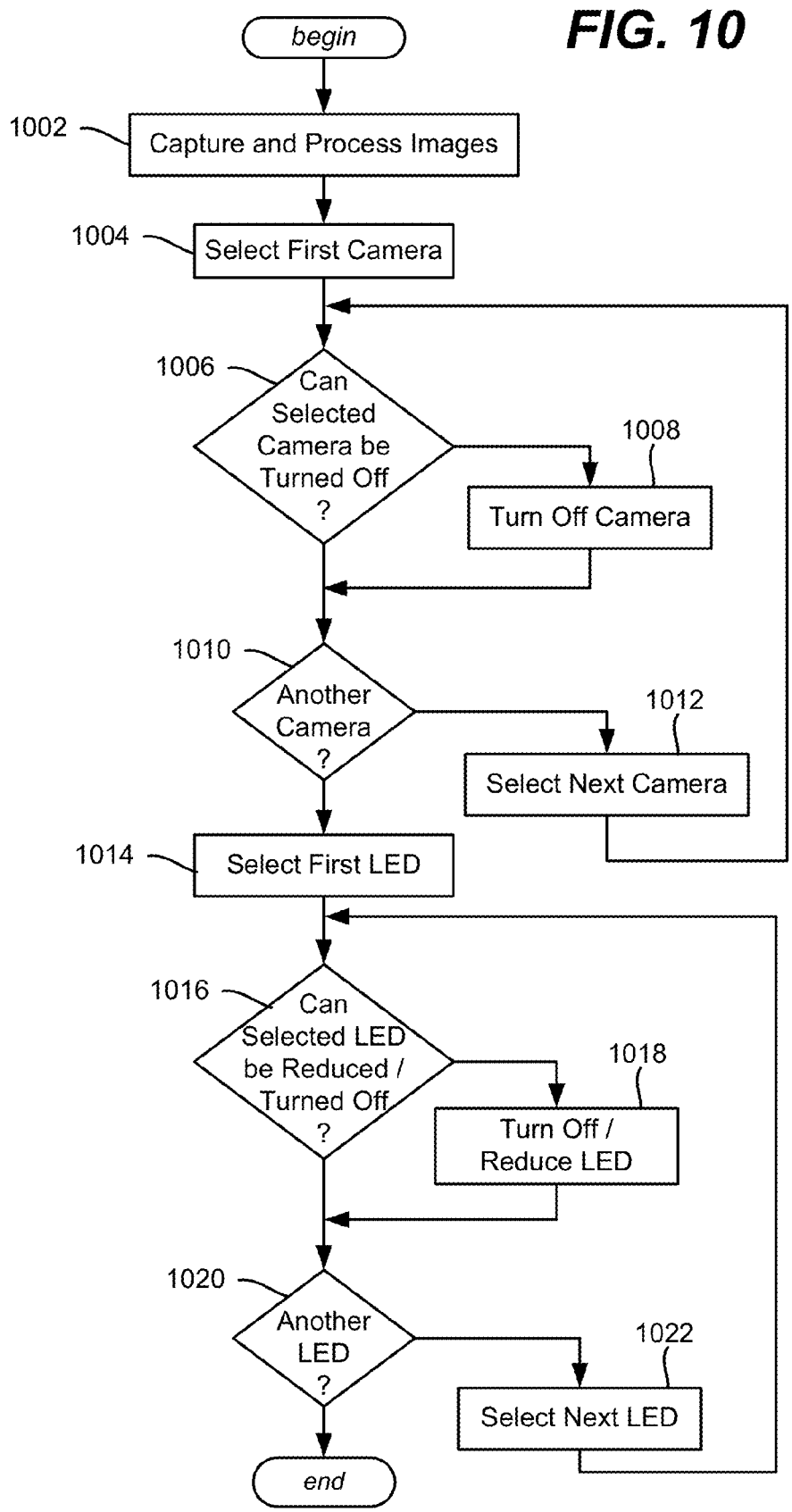
FIG. 10 is a flow diagram illustrating example steps that may be taken to selectively determine which cameras and/or light sources to use with respect to eye gaze detection, according to one or more example implementations.

FIG. 10 gives an example of some control logic, beginning at step 1002 where the images are captured and processed, e.g., a full set of cameras and LEDs may be initially used. The image processing may be to perform head tracking, general eye location, and/or may be based upon quality of the eye features, for example.

Via steps 1004, 1006, 1008 1010 and 1012, any camera that is not providing a useful image with respect to gaze detection (assuming it is not also used for another purpose) may be turned off in a multiple camera scenario. For instance, in the examples herein, a camera that is not seeing a subject's eye, such as the camera 332 of FIG. 3A is not providing a useful image. Similarly, an image that is not sufficiently sharp to detect the glints is not of use (although it may be useful to an extent if some detection is provided, and used for example in weighted averaging).

Steps 1014, 1016, 1018 1020 and 1022 provide a similar operation for LEDs, although these steps may reduce LED intensity for any LED rather than turn off the LED entirely. Thus, if an LED is not providing a glint, that LED may be turned off. If an LED is providing an undesirable reflection, that LED may be turned off;

Note that changing the LED states may change how the captured images appear, and thus some back-and-forth between LED state changes and which camera(s) to use may be performed to tune a given system for current conditions. Thus, some or all of the steps of FIG. 10 may be performed many times, such as periodically, upon some event (e.g., change in ambient light, significant head or device movement) or the like.

Figure 11:
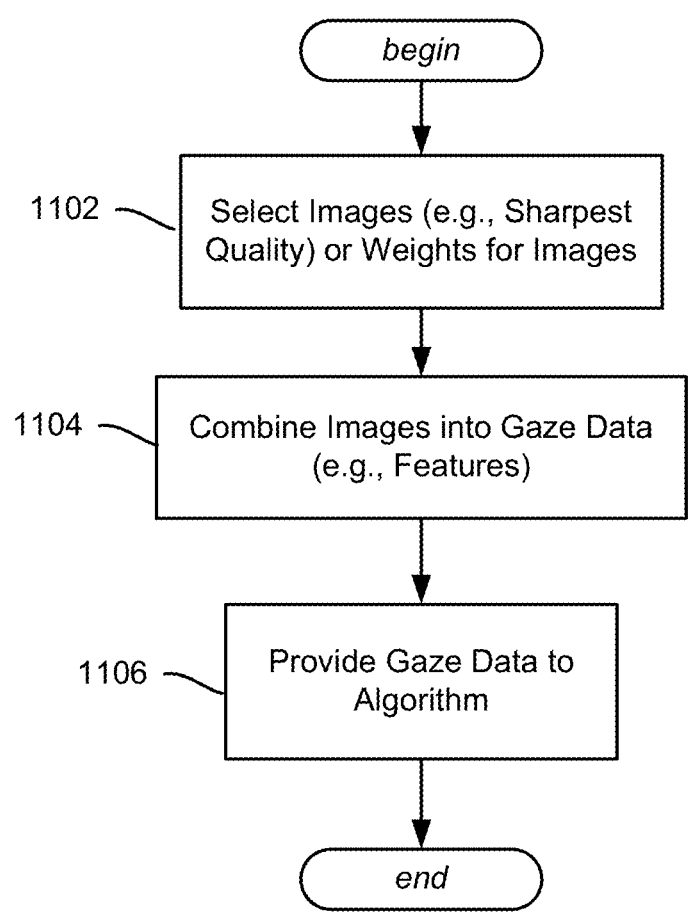
FIG. 11 is a flow diagram illustrating example steps that may be taken to combine images from multiple cameras for use in eye gaze detection, according to one or more example implementations.

FIG. 11 is generally directed towards the example combination of image data, beginning at step 1102 where those images that are sharpest with respect to capturing the eye (e.g., the desired features) are selected; the selection may associate a weight with each image, such as based upon sharpness.

Step 1104 combines these images into gaze data, e.g., averaged (using a weighted average corresponding to sharpness) for images that are useful. Step 1106 provides this gaze data to the gaze detection algorithm.

As can be seen, there is provided a unified framework for any number of cameras and any number of LEDs visible from each camera. The framework allows cameras and LEDs to be positioned and/or controlled for robust data collection regardless of the many variables that may exist in a given scenario, such as display tilt angle, display orientation, distance to the eye, ambient light conditions and so forth.

In one or more implementations, a plurality of cameras are positioned proximate a display, including a first camera on a first edge adjacent the display, and a second camera on a second edge adjacent the display, in which the second edge is not parallel to the first edge. At least one light source is configured to output light that generates corneal reflection data when reflected by an eye, and the cameras coupled to an image processing component to provide image data to the image processing component including captured corneal reflection data for use in eye gaze detection. The display may be incorporated into a device that is configured to change content rendering orientation of at least some displayed output in conjunction with a current orientation of the device.

The first camera may be embedded into the first edge and the second cameras embedded into the second edge. One or more light sources may be embedded into an edge adjacent the display. A plurality of infrared light sources may surround the first camera.

In one or more aspects, the cameras may be angled relative to the display, and angled differently relative to one another. The cameras may have different focal lengths relative to one another.

In one or more aspects, a controller may be configured to selectively turn off the first camera or the second camera. The controller may selectively turn off or reduce intensity of at least one of the infrared light sources.

In one or more implementations, three or more infrared light sources are configured to output light that generates corneal reflection data when reflected by an eye. A plurality of infrared-sensitive cameras is configured to capture the corneal reflection data for use in eye gaze detection. The cameras may provide image data including captured corneal reflection data to an image processing component.

One or more aspects are directed towards receiving image data corresponding to images of a human eye captured by at least two cameras. The image data may be combined into eye feature data that is provided to a gaze detection algorithm. Based upon at least one of the images, power to a light source may be reduced or turned off, and/or a camera may be turned off.

EXAMPLE OPERATING ENVIRONMENT

Figure 12:
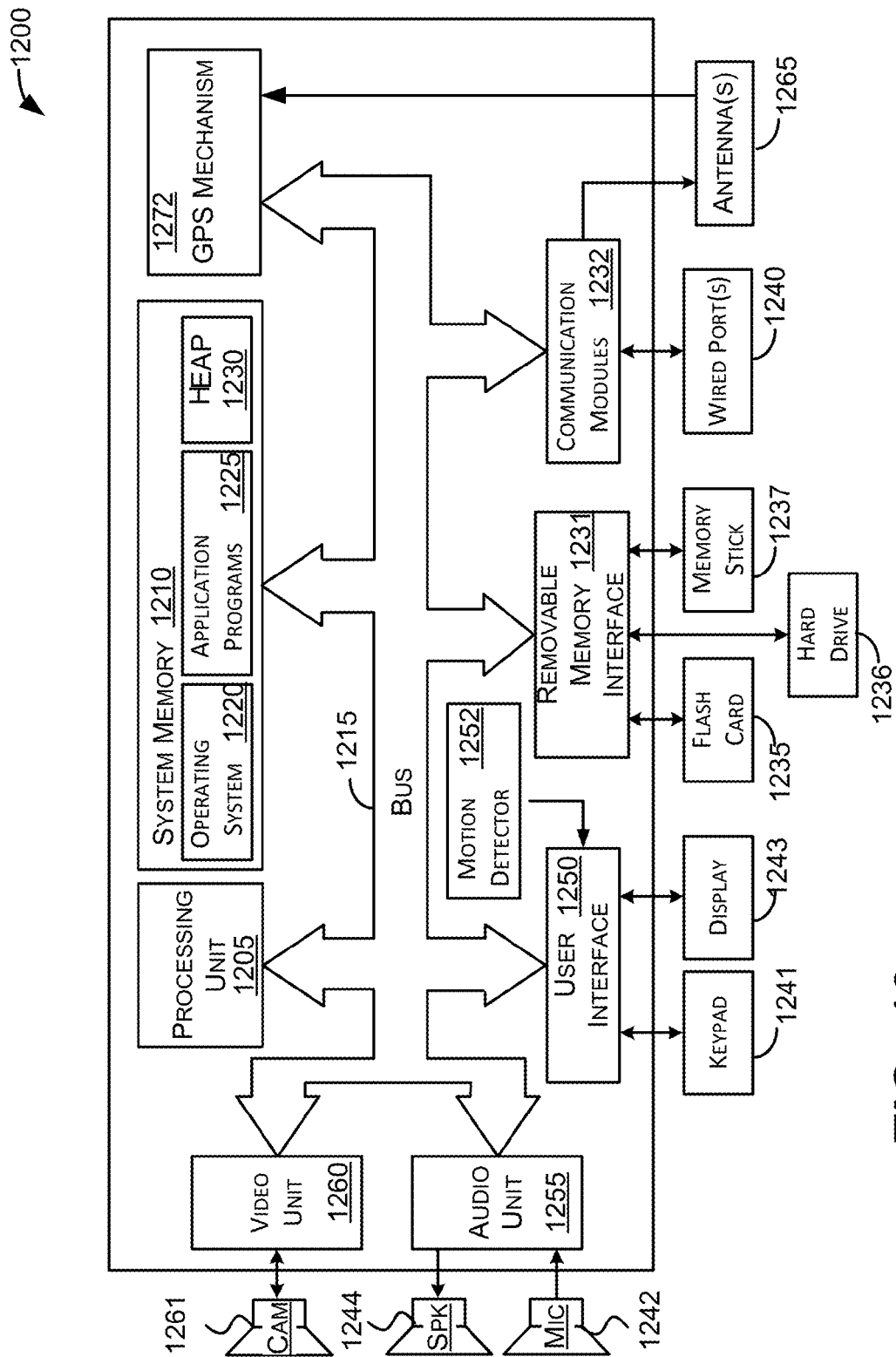
FIG. 12 is a block diagram representing an exemplary non-limiting computing system or operating environment, in the form of a mobile and/or handheld computing and/or communications device, into which one or more aspects of various embodiments described herein can be implemented.

FIG. 12 illustrates an example of a suitable mobile device 1200 on which aspects of the subject matter described herein may be implemented. The mobile device 1200 is only one example of a device and is not intended to suggest any limitation as to the scope of use or functionality of aspects of the subject matter described herein. Neither should the mobile device 1200 be interpreted as having any dependency or requirement relating to any one or combination of components illustrated in the example mobile device 1200. The mobile device may comprise a hand-held device such as a smartphone, tablet, laptop and so on.

With reference to FIG. 12, an example device for implementing aspects of the subject matter described herein includes a mobile device 1200. In some embodiments, the mobile device 1200 comprises a cell phone, a handheld device that allows voice communications with others, some other voice communications device, or the like. In these embodiments, the mobile device 1200 may be equipped with a camera for taking pictures, although this may not be required in other embodiments. In other embodiments, the mobile device 1200 may comprise a personal digital assistant (PDA), hand-held gaming device, notebook computer, printer, appliance including a set-top, media center, or other appliance, other mobile devices, or the like. In yet other embodiments, the mobile device 1200 may comprise devices that are generally considered non-mobile such as personal computers, servers, or the like.

Components of the mobile device 1200 may include, but are not limited to, a processing unit 1205, system memory 1210, and a bus 1215 that couples various system components including the system memory 1210 to the processing unit 1205. The bus 1215 may include any of several types of bus structures including a memory bus, memory controller, a peripheral bus, and a local bus using any of a variety of bus architectures, and the like. The bus 1215 allows data to be transmitted between various components of the mobile device 1200.

The mobile device 1200 may include a variety of computer-readable/machine-readable media. Such media can be any available media that can be accessed by the mobile device 1200 and includes both volatile and nonvolatile media, and removable and non-removable media. By way of example, and not limitation, computer-readable media may comprise computer storage media and communication media. Computer storage media includes volatile and nonvolatile, removable and non-removable media implemented in any method or technology for storage of information such as computer-readable instructions, data structures, program modules, or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by the mobile device 1200.

Communication media typically embodies computer-readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, Bluetooth®, Wireless USB, infrared, Wi-Fi, WiMAX, and other wireless media. Combinations of any of the above should also be included within the scope of computer-readable media.

The system memory 1210 includes computer storage media in the form of volatile and/or nonvolatile memory and may include read only memory (ROM) and random access memory (RAM). On a mobile device such as a cell phone, operating system code 1220 is sometimes included in ROM although, in other embodiments, this is not required. Similarly, application programs 1225 are often placed in RAM although again, in other embodiments, application programs may be placed in ROM or in other computer-readable memory. The heap 1230 provides memory for state associated with the operating system 1220 and the application programs 1225. For example, the operating system 1220 and application programs 1225 may store variables and data structures in the heap 1230 during their operations.

The mobile device 1200 may also include other removable/non-removable, volatile/nonvolatile memory. By way of example, FIG. 12 illustrates a flash card 1235, a hard disk drive 1236, and a memory stick 1237. The hard disk drive 1236 may be miniaturized to fit in a memory slot, for example. The mobile device 1200 may interface with these types of non-volatile removable memory via a removable memory interface 1231, or may be connected via a universal serial bus (USB), IEEE 12394, one or more of the wired port(s) 1240, or antenna(s) 1265. In these embodiments, the removable memory devices 1235-437 may interface with the mobile device via the communications module(s) 1232. In some embodiments, not all of these types of memory may be included on a single mobile device. In other embodiments, one or more of these and other types of removable memory may be included on a single mobile device.

In some embodiments, the hard disk drive 1236 may be connected in such a way as to be more permanently attached to the mobile device 1200. For example, the hard disk drive 1236 may be connected to an interface such as parallel advanced technology attachment (PATA), serial advanced technology attachment (SATA) or otherwise, which may be connected to the bus 1215. In such embodiments, removing the hard drive may involve removing a cover of the mobile device 1200 and removing screws or other fasteners that connect the hard drive 1236 to support structures within the mobile device 1200.

The removable memory devices 1235-437 and their associated computer storage media, discussed above and illustrated in FIG. 12, provide storage of computer-readable instructions, program modules, data structures, and other data for the mobile device 1200. For example, the removable memory device or devices 1235-437 may store images taken by the mobile device 1200, voice recordings, contact information, programs, data for the programs and so forth.

A user may enter commands and information into the mobile device 1200 through input devices such as a key pad 1241 and the microphone 1242. In some embodiments, the display 1243 may be touch-sensitive screen and may allow a user to enter commands and information thereon. The key pad 1241 and display 1243 may be connected to the processing unit 1205 through a user input interface 1250 that is coupled to the bus 1215, but may also be connected by other interface and bus structures, such as the communications module(s) 1232 and wired port(s) 1240. Motion detection 1252 can be used to determine gestures made with the device 1200.

A user may communicate with other users via speaking into the microphone 1242 and via text messages that are entered on the key pad 1241 or a touch sensitive display 1243, for example. The audio unit 1255 may provide electrical signals to drive the speaker 1244 as well as receive and digitize audio signals received from the microphone 1242.

The mobile device 1200 may include a video unit 1260 that provides signals to drive a camera 1261. The video unit 1260 may also receive images obtained by the camera 1261 and provide these images to the processing unit 1205 and/or memory included on the mobile device 1200. The images obtained by the camera 1261 may comprise video, one or more images that do not form a video, or some combination thereof.

The communication module(s) 1232 may provide signals to and receive signals from one or more antenna(s) 1265. One of the antenna(s) 1265 may transmit and receive messages for a cell phone network. Another antenna may transmit and receive Bluetooth® messages. Yet another antenna (or a shared antenna) may transmit and receive network messages via a wireless Ethernet network standard.

Still further, an antenna provides location-based information, e.g., GPS signals to a GPS interface and mechanism 1272. In turn, the GPS mechanism 1272 makes available the corresponding GPS data (e.g., time and coordinates) for processing.

In some embodiments, a single antenna may be used to transmit and/or receive messages for more than one type of network. For example, a single antenna may transmit and receive voice and packet messages.

When operated in a networked environment, the mobile device 1200 may connect to one or more remote devices. The remote devices may include a personal computer, a server, a router, a network PC, a cell phone, a media playback device, a peer device or other common network node, and typically includes many or all of the elements described above relative to the mobile device 1200.

Aspects of the subject matter described herein are operational with numerous other general purpose or special purpose computing system environments or configurations. Examples of well known computing systems, environments, and/or configurations that may be suitable for use with aspects of the subject matter described herein include, but are not limited to, personal computers, server computers, hand-held or laptop devices, multiprocessor systems, microcontroller-based systems, set top boxes, programmable consumer electronics, network PCs, minicomputers, mainframe computers, distributed computing environments that include any of the above systems or devices, and the like.

Aspects of the subject matter described herein may be described in the general context of computer-executable instructions, such as program modules, being executed by a mobile device. Generally, program modules include routines, programs, objects, components, data structures, and so forth, which perform particular tasks or implement particular abstract data types. Aspects of the subject matter described herein may also be practiced in distributed computing environments where tasks are performed by remote processing devices that are linked through a communications network. In a distributed computing environment, program modules may be located in both local and remote computer storage media including memory storage devices.

Furthermore, although the term server may be used herein, it will be recognized that this term may also encompass a client, a set of one or more processes distributed on one or more computers, one or more stand-alone storage devices, a set of one or more other devices, a combination of one or more of the above, and the like.

CONCLUSION

While the invention is susceptible to various modifications and alternative constructions, certain illustrated embodiments thereof are shown in the drawings and have been described above in detail. It should be understood, however, that there is no intention to limit the invention to the specific forms disclosed, but on the contrary, the intention is to cover all modifications, alternative constructions, and equivalents falling within the spirit and scope of the invention.

In addition to the various embodiments described herein, it is to be understood that other similar embodiments can be used or modifications and additions can be made to the described embodiment(s) for performing the same or equivalent function of the corresponding embodiment(s) without deviating therefrom. Still further, multiple processing chips or multiple devices can share the performance of one or more functions described herein, and similarly, storage can be effected across a plurality of devices. Accordingly, the invention is not to be limited to any single embodiment, but rather is to be construed in breadth, spirit and scope in accordance with the appended claims.

What is claimed is:

1. A system comprising:
  a display;
  a plurality of cameras positioned proximate the display, the plurality of cameras comprising:
    a first camera on a first edge adjacent the display; and
    a second camera on a second edge adjacent the display;
  at least one light source configured to output light that generates corneal reflections when reflected by an eye;
  an image processing component coupled to the plurality of cameras, the image processing component configured to:
    receive from the first camera a first image of the eye captured by the first camera; and
    receive from the second camera a second image of the eye captured by the second camera, the first and second images comprising the corneal reflections for use by the image processing component in eye gaze detection; and
  a controller configured to selectively turn off one of the first and second cameras based on a sharpness detection of the first and second images of the eye by the image processing component.

2. The system of claim 1, wherein the display is incorporated into a device that is configured to change content rendering orientation of at least some displayed output in conjunction with a current orientation of the device.

3. The system of claim 1, wherein the plurality of cameras are angled relative to the display, and wherein the first and second cameras are angled differently relative to one another.

4. The system of claim 1, wherein the first and second cameras have different focal lengths relative to one another.

5. The system of claim 1, wherein the first camera is embedded into the first edge and the second camera is embedded into the second edge.

6. The system of claim 1, wherein the at least one light source is embedded into an edge adjacent the display.

7. The system of claim 1, wherein the display is incorporated into one of the following: a tablet computing device, a laptop computer, a smartphone, or a handheld computing device.

8. The system of claim 1, wherein the display is incorporated into one of the following: a television or a computer monitor.

9. The system of claim 1, wherein the at least one light source comprises a plurality of infrared light sources, and wherein the controller is further configured to selectively turn off or reduce an intensity of at least one of the plurality of infrared light sources.

10. The system of claim 1, wherein the at least one light source and the first camera comprises a unitary assembly, the at least one light source comprising a plurality of infrared light sources that surround the first camera.

11. The system of claim 1, wherein the second edge is not parallel to the first edge.

12. A system comprising:
a plurality of infrared light sources, the plurality of infrared light sources configured to output infrared light that generates corneal reflections when reflected by an eye;
a plurality of infrared-sensitive cameras, the plurality of infrared-sensitive cameras configured to capture the corneal reflections as a plurality of images of the eye for use in eye gaze detection; and
a controller configured to selectively turn off at least one infrared-sensitive camera of the plurality of infrared-sensitive cameras based on a sharpness detection of respective images of the plurality of images of the eye.

13. The system of claim 12 further comprising an image processing component, wherein the plurality of infrared-sensitive cameras are coupled to the image processing component to provide the plurality of images of the eye to the image processing component.

14. The system of claim 12, wherein at least two of the plurality of infrared-sensitive cameras are angled differently relative to one another.

15. The system of claim 12, wherein at least two of the plurality of infrared-sensitive cameras have different focal lengths relative to one another.

16. The system of claim 12, wherein the controller is further configured to reduce an intensity of at least one of the plurality of infrared light sources.

17. The system of claim 12, wherein the plurality of infrared-sensitive cameras comprise two infrared-sensitive cameras located on a common edge adjacent a display.

18. A method comprising:
receiving image data corresponding to a plurality of images of a human eye, the plurality of images captured by at least two cameras;
combining the image data into eye feature data;
providing the eye feature data to a gaze detection algorithm;
determining a sharpness of respective images of the plurality of images; and
based on the sharpness determination, selectively turning off one of the at least two cameras.

19. The method of claim 18 further comprising:
turning off or reducing power to a light source based upon a quality of the eye feature data captured in the respective images of the plurality of images.

20. The method of claim 18 further comprising:
projecting light onto the human eye using at least one light source, the light generating corneal reflections when reflected by the human eye.

* * * * *